United States Patent [19]

Lerner

[11] 4,006,252

[45] Feb. 1, 1977

[54] METHODS AND COMPOSITIONS FOR REDUCING PLASMA LIPID LEVELS

[75] Inventor: Sidney I. Lerner, Cincinnati, Ohio

[73] Assignee: Ethyl Corporation, Richmond, Va.

[22] Filed: May 12, 1972

[21] Appl. No.: 252,582

Related U.S. Application Data

[60] Continuation-in-part of Ser. No. 647,582, May 8, 1967, abandoned, which is a division of Ser. No. 324,255, Nov. 18, 1963, abandoned.

[52] U.S. Cl. .............................................. 424/331
[51] Int. Cl.$^2$ ....................................... A61K 31/12
[58] Field of Search ................................... 424/331

[56] References Cited

OTHER PUBLICATIONS

Wilson–Grisvold, Textbook of Organic Medicinal & Pharmaceutical Chemistry, 4th Ed., 1962, p. 632.
Chemical Abstracts 57:8679a (1962).

Primary Examiner—Leonard Schenkman
Attorney, Agent, or Firm—Donald L. Johnson; John F. Sieberth; Robert A. Linn

[57] ABSTRACT

Plasma lipid levels are reduced by treating mammalian subjects with a semiquinone such as (3,5-di-tert-butyl-4-oxo-2,5-cyclohexadien-1-ylidene)-(3,5-di-tert-butyl-4-hydroxyphenyl)methane.

6 Claims, No Drawings

METHODS AND COMPOSITIONS FOR REDUCING PLASMA LIPID LEVELS

CROSS-REFERENCES TO RELATED APPLICATIONS

This application is a continuation-in-part of now abandoned application Ser. No. 647,582, filed May 8, 1967, which in turn is a division of application Ser. No. 324,255, filed Nov. 18, 1963, and now abandoned.

This invention relates to a method and composition for reducing plasma lipid levels and particularly cholesterol, triglyceride and phospholipid levels.

Prior to this invention there has been a great need for an effective antihyperlipemic agent which is low in toxicity and is relatively free of undesirable side effects. For example, it is believed that coronary artery disease and atherosclerosis in man are associated with an abnormally high concentration of cholesterol and other lipids in the blood stream. Of particular significance is the concentration of the β-lipoprotein fraction in the blood. The reduction of the amount of these lipids, including not only free and esterified cholesterol, but also phospholipids and triglycerides, is of major importance in the prevention and treatment of coronary artery disease, atherosclerosis, other vascular and heart ailments and disorders of lipid metabolism.

It is therefore an object of this invention to provide a method for reducing plasma lipid levels, particularly cholesterol, triglyceride and phospholipid levels. Another object is to provide a pharmeceutical composition capable of lowering plasma lipid levels when internally administered. A further object is to provide such reductions with a minimum of untoward side effects.

According to one embodiment of this invention, the above and other objects are accomplished by providing a method of lowering plasma lipid levels which comprises internally administering an (oxocyclohexadien-1-ylidene)-(hydroxyphenyl) methane in an amount sufficient to lower the plasma lipid level. The term "(oxocyclohexadien-1-ylidene)-(hydroxyphenyl) methane" includes those compounds where the carbon atom connecting the phenyl group and the cyclohexadien-1-ylidene group may be additionally substituted with a hydrocarbyl group. (Oxocyclohexadien-1-ylidene)-(hydroxyphenyl) methanes in general are useful in this invention and may be represented by one of the following formulas:

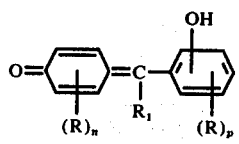

I.

or

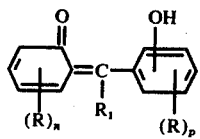

II.

wherein $R_1$ is selected from the group consisting of hydrogen and hydrocarbon radicals, R is a hydrocarbon radial and $n$ and $p$ are integers of from 0–4, such that when $n$ and $p$ are each at least 1, the radicals collectively represented by R may be the same or different. Formula I represents (4-oxo-2,5-cyclohexadien-1-ylidene)-(hydroxyphenyl) methane and Formula II represents (2-oxo-3,5-cyclohexadien-1-ylidene)-(hydroxyphenyl) methanes. The hydrocarbon radicals are preferably alkyl of from 1–12 carbon atoms, cycloalkyl of from 6 to 12 carbon atoms, aryl of from 6–12 carbon atoms and aralkyl of from 7–12 carbon atoms. Examples of such (oxocyclohexadien-1-ylidene)-(hydroxyphenyl) methanes include (4-oxo-2,5-cyclohexadien-1-ylidene)-(4-hydroxyphenyl) methane, (2-oxo-3,5-cyclohexadien-1-ylidene)-(2-hydroxyphenyl) methane, (3,5-di-tert-butyl-4-oxo-2,5-cyclohexadien-1-ylidene)-(3,5-di-tert-butyl-4-hydroxyphenyl)-methyl methane, (3-tert-butyl-5-methyl-4-oxo-2,5-cyclohexadien-1-ylidene)-(3-tert-butyl-4-hydroxy-5-methylphenyl)-methyl methane, (3,5-di-tert-butyl-4-oxo-2,5-cyclohexadien-1-ylidene)-(3-tert-butyl-4-hydroxy-5-methylphenyl) methane, (3-tert-butyl-5-methyl-4oxo-2,5-cyclohexadien-1-ylidene)-(3,5-di-tert-butyl-4-hydroxyphenyl) methane, (2-ethyl-4-oxo-2,5-cyclohexadien-1-ylidene)-(2-ethyl-4-hydroxyphenyl)-methyl methane, (2-oxo-3,5-cyclohexadien-1-ylidene)-[3-(2-hexyl)-4-hydroxy-5,6-dimethylphenyl]-n-propyl methane, (4-oxo-2,5-cyclohexadien-1-ylidene)-(3-sec-butyl-5-hydroxyphenyl)-n-butyl methane, (3-cyclohexyl-6-methyl-4-oxo-2,5-cyclohexadien-1-ylidene)-[2-(α-methylbenzyl)-5-(p-methylcyclohexyl-4,6-diethyl-3-hydroxyphenyl]-n-hexyl methane, [2,6-dimethyl-3-(p-n-amylphenyl)-5-n-undecyl-4-oxo-2,5-cyclohexadien-1-ylidene]-[3-(α,α-dimethylbenzyl)-4-hydroxy-5-(o-methylphenyl)phenyl]-(2'-amyl) methane, (4-oxo-2,5-cyclohexadien-1-ylidene)- [3-(α,α-dimethyl-m-methylbenzyl)-4-hydroxyphenyl]-ethyl methane, [3-(α-n-propyl-α-methylbenzyl)-6-(3'-dodecyl)-2-oxo-3,5-cyclohexadien-1-ylidene]-[3-(α-n-propyl-α-ethylbenzyl)-6-hydroxy-5-isopropylphenyl]-n-hexyl methane, (4-α-methylbenzyl-2-oxo-3,5-cyclohexadien-1-ylidene-[3-hydroxy-2,5-diisobutyl-4-(n-ethylphenyl)-phenyl]-phenyl methane, [3-(di-o-ethylcyclohexyl)-(5-n-nonyl-4-oxo-2,5-cyclohexadien-1-ylidene)-(2-hydroxyphenyl)-(α,α-diethyl-o-methylbenzyl) methane, (3-n-amyl-5,6-dimethyl-4-oxo-2,5-cyclohexadien-1-ylidene)-(4-hydroxyphenyl)-benzyl methane, [3-(3'-heptyl-4-oxo-2,5-cyclohexadien-1-ylidene]-[2-hydroxy-5-methyl-3-(p-n-butylphenyl) phenyl]-n-butyl methane, (3,5-di-tert-butyl-4-oxo-2,5-cyclohexadien-1-ylidene)-(2-hydroxy-3-isopropyl-5-phenylphenyl)-(p-n-hexylphenyl) methane, (6-n-propyl-4-oxo-2,5-cyclohexadien-1-ylidene)-[3-n-decyl-4-hydroxy-5-(3'-undecyl)phenyl]cyclohexyl methane, [4-(p-n-propylphenyl)-2-oxo-3,5-cyclohexadien-1-ylidene]-(2-hydroxy-3-octyl-5-n-propylphenyl)-[4-(p-n-propylcyclohexyl)-3-hydroxy-6-isopropyl]-n-propyl methane, (3,5-dimethyl-4-oxo-2,5-cyclohexadien-1-ylidene)-[3-(2'-dodecyl)-5-ethyl-6-hydroxyphenyl)-(p-n-hexylcyclohexyl) methane and (2,3,5,6-tetramethyl-4-oxo-2,5-cyclohexadien-1-ylidene)-(4-hydroxy-2,3,5,6-tetramethylphenyl) methane. In addition, all of the (oxocyclohexadien-1-ylidene)-(hydroxyphenyl) methanes obtained by partial oxidation of the di-(hydroxyphenyl) methanes disclosed in U.S. Pat. Nos. 2,807,653 and 2,829,175 including their isomers and homelogues, are examples.

In another embodiment of this invention I provide a composition having anticholesterinemic and antilipemic activity comprising a suitable pharmaceutical carrier and a pharmaceutically effective amount of an (oxocyclohexadien-1-ylidene)-(hydroxyphenyl) methane as described above.

While (oxocyclohexadien-1-ylidene)-(hydroxyphenyl) methanes in general are useful, certain structures are preferred. Preferred (oxocyclohexadien-1-ylidene)-(hydroxyphenyl) methanes are those of Formula I and II in which n and p are each at least 1, the hydrocarbon substituents on the phenyl group are the same as the hydrocarbon substituents on the cyclohexadiene group and in the same position relative to the carbon atom connecting the phenyl group and the cyclohexadien-1-ylidene group, the hydroxyl group is in a position selected from ortho and para to the cyclohexadiene group and the hydroxyl group and oxo group are in the same positions relative to the carbon atom connecting the phenyl group to the cyclohexadien-1-ylidene group. The preferred compounds are, therefore, (hydrocarbyl-4-oxo-2,5-cyclohexadien-1-ylidene)-(4-hydroxyhydrocarbylphenyl) methanes and (hydrocarbyl-2-oxo-3,5-cyclohexadien-1-ylidene)-(2-hydroxyhydrocarbylphenyl) methanes. Examples of such compounds include (3,5-di-tert-butyl-4-oxo-2,5-cyclohexadien-1-ylidene)-(3,5-di-tert-butyl-4-hydroxyphenyl)-phenyl methane, (3,5-di-tert-butyl-2-oxo-3,5-cyclohexadien-1-ylidene)-(3,5-di-tert-butyl-2-hydroxyphenyl) methane, (3,5-di-tert-butyl-6-methyl-2-oxo-3,5-cyclohexadien-1-ylidene)-(3,5-di-tert-butyl-2-hydroxy-6-methylphenyl) methane, (3-tert-butyl-5ethyl-2-oxo-3,5-cyclohexadien-1-ylidene)-(3-tert-butyl-5-ethyl-2-hydroxyphenyl) methane, (3-tert-butyl-5-methyl-2-oxo-3,5-cyclohexadien-1-ylidene)-(3-tert-butyl-5-methyl-2-hydroxyphenyl) methane, (5-methyl-2-oxo-3,5-cyclohexadien-1-ylidene)-(2-hydroxy-5-methylphenyl)-n-propyl methane, (3-cyclohexyl-4-oxo-5-phenyl-2,5-cyclohexadien-1-ylidene)-(3-cyclohexyl-4-hydroxy-5-phenylphenyl)-(m-ethylphenyl) methane, [3-methyl-5(3'-naphthyl)-4-oxo-2,5-cyclohexadien-1-ylidene]-[4-hydroxy-3-methyl-5-(3'-naphthyl)-phenyl]-(m-n-propylcyclohexyl) methane, [4-(α,α-dimethylbenzyl)-2-oxo-3,5-cyclohexadien-1-ylidene]-[4-(α,α-di-methylbenzyl)-2-hydroxyphenyl]-(2'-hexyl) methane, [3-m-n-amylcyclohexyl)-5-(p-methylphenyl)-4-oxo-2,5-cyclohexadien-1-ylidene]-[3-(m-n-amylcyclohexyl)-4-hydroxy-5-(p-methylphenyl)-phenyl]-(α-n-propylbenzyl) methane, (3-sec-butyl-5-phenyl-2-oxo-3,5-cyclohexadien-1-ylidene)-(3-sec-butyl-2-hydroxy-5-phenylphenyl) methane, [4-(α-methylbenzyl)-2-oxo-3,5-cyclohexadien-1-ylidene]-[4-(α-methyl-benzyl)-2-hydroxyphenyl]-n-amyl methane, [3-(2'-hexyl)-5-(2'-nonyl)-2-oxo-3,5-cyclohexadien-1-ylidene]-[3-(2'-hexyl)-2-hydroxy-5-(2'-nonyl)-phenyl] methane, [3-(2'-dodecyl)-5-isopropyl-4-oxo-2,5-cyclohexadien-1-ylidene]-[3-(2'-dodecyl)-4-hydroxy-5-isopropylphenyl]-n-butyl methane, (3-tert-butyl-4-oxo-2,5-cyclohexadien-1-ylidene)-(3-tert-butyl-4-hydroxyphenyl) methane, (3-tert-butyl-2-oxo-3,5-cyclohexadien-1-ylidene)-(3,5-di-tert-amyl-4-hydroxyphenyl)-n-propyl-methane.

It is further preferred that the compounds have the formula:

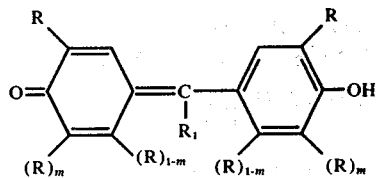

wherein R is as defined above following Formulas I and II, $R_1$ is selected from hydrogen and alkyl of from 1–6 carbon atoms and m is selected from 0 and 1. Formula III represents a (3-hydrocarbyl-5 or 6-hydrocarbyl-4-oxo-2,5-cyclohexadien-1-ylidene)-(3-hydrocarbyl-5 or 6-hydrocarbyl-4-hydroxyphenyl) methane. Such compounds are preferred as they are even easier to prepare and generally more effective than the other compounds. Examples of such compounds include [3,5-di(α-methylbenzyl)-4-oxo-2,5-cyclohexadien-1-ylidene]-[3,5-di-(α-methylbenzyl)-4-hydroxyphenyl] methane, (3-cyclohexyl-5-methyl-4-oxo-2,5-cyclohexadien-1-ylidene)-(3-cyclohexyl-4-hydroxy-5-methylphenyl) methane, (3,5-dicyclohexyl-4-oxo-2,5-cyclohexadien-1-ylidene)-(3,5-dicyclohexyl-4-hydroxyphenyl) methane, (3-tert-butyl-5-methyl-4-oxo-2,5-cyclohexadien-1-ylidene)-(3-tert-butyl-4-hydroxy-5-methylphenyl)-n-propyl methane, [3-(α-methylbenzyl)-5-tert-butyl-4-oxo-2,5-cyclohexadien-1-ylidene]-[3-(α-methylbenzyl)-5-tert-butyl-4-hydroxyphenyl] methane, (3-tert-butyl-5-methyl-4-oxo-2,5-cyclohexadien-1-ylidene)-(3-tert-butyl-4-hydroxy-5-methylphenyl)-phenyl methane, (2-cyclohexyl-5-methyl-4-oxo-2,5-cyclohexadien-1-ylidene)-(2-cyclohexyl-4-hydroxy-5-methylphenyl) methane, [3-(2'-dodecyl)-6-ethyl-4-oxo-2,5-cyclohexadien-1-ylidene]-[3-(2'-dodecyl)-6-ethyl-4-hydroxyphenyl]-methane, [3-(2'-decyl)-4-oxo-5-phenyl-2,5-cyclohexadien-1-ylidene)-[3-(2'-decyl)-4-hydroxy-5-phenylphenyl]-methyl methane, [3-(α-methylbenzyl)-5-n-heptyl-4-oxo-2,5-cyclohexadien-1-ylidene)-[3-(α-methylbenzyl)-5-n-heptyl-4-hydroxyphenyl] methane, [3-(α,α-diethylbenzyl)-5-(p-n-butylcyclohexyl)-4-oxo-2,5-cyclohexadien-1-ylidene]-[3-(α,α-diethylbenzyl-5-(p-n-butylcyclohexyl)-4-hydroxyphenyl]-n-butyl methane, [2-(2'-octyl)-4-oxo-5-(2'undecyl)-2,5-cyclohexadien-1-ylidene]-4-hydroxy-2-(2'-octyl)-5-(2'-undecyl)-phenyl]-methyl methane, [2-(o-ethylcyclohexyl)-4-oxo-5-(m-n-propylphenyl)-2,5-cyclohexadien-1-ylidene]-[2-(o-ethylocyclohexyl)-4-hydroxy-5-(m-n-propylphenyl)phenyl] methane, [2-(α-methylbenzyl)-5-(2'-octyl)-4-oxo-2,5-cyclohexadien-1-ylidene]-[2-(α-methylbenzyl)-4-hydroxy-5-(2'-octyl)phenyl]-n-butyl methane, [3-(α-ethyl-α-methylbenzyl)-5-(2'-napthyl)-4-oxo-2,5-cyclohexadien-1-ylidene]-[3-(α-ethyl-α-methylbenzyl)-4-hydroxy-5-(2'-naphthyl)phenyl]-ethyl methane and [3-(α-ethyl-α-n-propylbenzyl)-5-(2'-hexyl)-4-oxo-2,5-cyclohexadien-1-ylidene]-[3-(α-ethyl-α-n-propylbenzyl)-5-(2'-hexyl)-4-hydroxyphenyl)-n-hexyl methane. Those compounds of Formula in which m is 1 are particularly preferred; that is a (3,5-di-hydrocarbyl-4-oxo-2,5-cyclohexadien-1-ylidene)-(3,5-di-hydrocarbyl-4-hydroxyphenyl) methane.

In all of the above embodiments it is further preferred that R be an alkyl radical of from 1–12 carbon atoms and that where $R_1$ is a hydrocarbon radical, it be an alkyl radical of from 1–6 carbon atoms. Referring to Formula III, it is still further preferred that at least one of the R's on the phenyl group that is ortho to the hydroxyl group, and at least one of the R's on the cyclohexadien-1-ylidene group that is ortho to the oxo group, have at least 3 carbon atoms and be branched on the alpha carbon atom. Such compounds are generally more effective, and this may be due at least in part to the fact that such compounds are sterically hindered. Examples of such compounds include (3,5-di-tert-butyl-4-oxo-2,5-cyclohexadien-1-ylidene)-(3,5-di-tert-butyl-4-hydroxyphenyl)-n-propyl methane, 3,5-di-tert-butyl-4-oxo-2,5-cyclohexadien-1-ylidene)-(3,5-di-tert-butyl-4-hydroxyphenyl)-methyl methane, (3-tert-butyl-5-methyl-4-oxo-2,5-cyclohexadien-1-ylidene)-(3-tert-butyl-4-hydroxy-5-methylphenyl)-methyl methane, (3-tert-butyl-5-methyl-4-oxo-2,5-cyclohexadien-1-ylidene)-(3-tert-butyl-4-hydroxy-5-methylphenyl)-n-propyl methane, (3,5-di-tert-butyl-4-oxo-2,5-cyclohexadien-1-ylidene)-(3,5-di-tert-butyl-4-hydroxyphenyl)-ethyl methane, (2,5-di-tert-butyl-4-oxo-2,5-cyclohexadien-1-ylidene)-(2,5-di-tert-butyl-4-hydroxyphenyl) methane, (2-tert-butyl5-isopropyl-4-oxo-2,5-cyclohexadien-1-ylidene)-(2-tert-butyl-4-hydroxy-5-isopropylphenyl) methane, (3-tert-butyl-6-isopropyl-4-oxo-2,5-cyclohexadien-1-ylidene)-(3-tert-butyl-4-hydroxy-6-isopropylphenyl) methane, [3-methyl-4-oxo-3-(2'undecyl)-2,5-cyclohexadien-1-ylidency]-[4-hydroxy-3-methyl-5-(2'-undecyl) phenyl]-methyl methane, (3-tertamyl-5-ethyl-4-oxo-2,5-cyclohexadien-1-ylidene]-(3-tert-amyl-5- ethyl-4-hydroxyphenyl)-ethyl methane, [3-(2'-heptyl)-5-(3'-octyl)-4-oxo-2,5-cyclohexadien-1-ylidene]-[3-(2'-heptyl)-4-hydroxy-5-(3'-octyl)-phenyl]methane, [3,5-di-(2'dodecyl)-4-oxo-2,5-cyclohexadien-1-ylidene]-[3,5-di-(2'-dodecyl)-4-hydroxyphenyl]-m-hexyl methane, (3-tert-amyl-5-tert-butyl-4-oxo-2,5-cyclohexadien-1-ylidene)-(3-tert-amyl-5-tert-butyl-4-hydroxyphenyl) methane, [3-(3'-undecyl)-5-(2'-nonyl)-4-oxo-2,5-cyclohexadien-1-ylidene]-[4-hydroxy-3-(3'-undecyl)-5-(2'-npnyl)-phenyl]-n-amyl methane and (3,6-diisopropyl-4-oxo-2,5-cyclohexadien-1-ylidene)-(4-hydroxy-3,6-diisopropylphenyl) methane.

The most particularly preferred group of compounds have the formula:

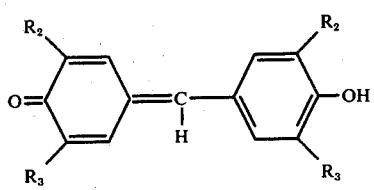

IV wherein R₂ is an alpha-branched alkyl radical of from 3–12 carbon atoms and R₂ is an alkyl radical of from 1–12 carbon atoms. Formula IV represents a (3-alkyl-5-alpha-branched-alkyl-4-oxo-2,5-cyclohexadien-1-ylidene)-(3-alkyl-5-alpha-branched-alkyl-4-oxo-2,5-cyclohexadien-1-ylidene)-(3-alkyl-5-alpha-branched-alkyl-4-hydroxyphenyl) methane. These compounds are the most effective and most economically prepared. Examples of such compounds include (3,5-di-tert-butyl-4-oxo-2,5-cyclohexadien-1-ylidene)-3,5-di-tert-butyl-4-butyl-4-hydroxyphenyl) methane, (3,5-diisopropyl-4-oxo-2,5-cyclohexadien-1-ylidene)-(4-hydroxy-3,5-diisopropylphenyl) methane, (3-tert-butyl-5-methyl-4-oxo-2,5-cyclohexadien-1-ylidene)-(3-tert-butyl-4-hydroxy-5-methylphenyl) methane, [3-(1', 1', 3', 3'-tetramethylbutyl)-5-methyl-4-oxo-2,5-cyclohexadien-1-ylidene]-[4-hydroxy-3-(1', 1', 3', 3'-tetramethylbutyl)-5-methylphenyl]methane, (3-tert-butyl-5-isopropyl-4-oxo-2,5-cyclohexadien-1-ylidene)-(3-tert-butyl-4hydroxy-5-isopropylpheryl) methane, (3,5-di-sec-butyl-4-oxo-2,5-cyclohexadien-1-ylidene)-(3,5-di-sec-butyl-4-hydroxyphenyl) methane, (3-isopropyl-5-methyl-4-oxo-2,5-cyclohexadien-1-ylidene)-(4-hydroxy-3-isopropyl-5-methylphenyl) methane, [3-(2'-amyl)-5-ethyl-4-oxo-2,5-cyclohexadien-1-ylidene)-[3-(2'-amyl)-5-ethyl-4-hydroxyphenyl]methane, [3-(2'-heptyl)-5-(3'-octyl)-4-oxo-2,5-cyclohexadien-1-ylidene]-[3-(2'-heptyl)-4-hydroxy-5-(3'-octyl)-phenyl]methane, [3-(2'-hexyl)-5-n-nonphenyl-4-oxo-2,5-cyclohexadien-1-ylidene]-[3-(2'-hexyl)-4-hydroxy-5-n-nonylphenyl]methane, [3-tert-butyl-5-(3'-undecyl)-4-oxo-2,5-cyclohexadien-1-yliden]-[3-tert-butyl-4-hydroxy-5-(3'-undecyl) phenyl]methane and (3,5-di-tert-amyl-4-oxo-2,5-cyclohexadien-1-ylidene-(3,5-di-tert-amyl-4-hydroxyphenyl) methane.

The most particularly preferred compound is (3,5di-tert-butyl-4-oxo-2,5-cyclohexadien-1-ylidene)-(3,5-di-tert-butyl-4-hydroxyphenyl) methane. This compound has outstanding effectiveness in lowering circulating blood lipid levels, particularly the 8-lipoprotein fraction.

The compounds of this invention can be prepared by various methods. Those (oxocyclohexadien-1-ylidene)-(hydroxyphenyl) methanes in which the substituents in the phenyl group are the same as that in the cyclohexadien-1-ylidene group can be prepared by condensation of an appropriate phenol with an appropriate aldehyde, in the presence of base, as described in U.S. Pat. No. 2,807,653, followed by oxidation to the hemiquinoid or semiquinone state. This method can also be used to prepare those 2-(hydroxyphenyl) methanes in which the substituents on the phenyl group and on the cyclohexadien-1-ylidene group are different. In these cases two different phenols are condensed with an appropriate aldehyde, using an appropriate condensation procedure, and ordinary separation procedures, such as fractional distillation, crystallization and solvent extraction procedures etc., can be used. Oxidation of the bisphenol will then produce the hemiquinoid and semiquinone structure.

To obtain the desired (oxocyclohexadien-1-ylidene)-(hydroxyphenyl) methane, di-(hydroxyphenyl) methane can be treated with bromine in glacial acetic acid to form a monobrominated product which can then be dehydrobrominated in ethanolic alkali and subsequently neutralized to give the desired (oxocyclohexadien-1-ylidene)-(hydroxyphenyl) methane. If the structure of the di-(hydroxyphenyl) methane is not symmetrical, then the resultant mixture of (oxocyclohexadien-1-ylidene)-(hydroxyphenyl) methanes can be used as such or they can be separated by the procedures described above for separation of mixed di-(hydroxyphenyl) methanes.

The compounds of this inventon are remarkably effective in bringing about a rapid drop in circulating serum lipid levels using very low dosage regimens. This allows use in pharmaceutical forms which are both convenient for administration and pleasant for patient consumption.

To demonstrate the outstanding effectiveness of the compounds of this invention, and by way of example, tests are performed on dogs (Beagles) which are separated into four groups. The Control Group is maintained on a diet of Allied Mills - Tail Wagger Dog Food-Krums to which is added 5.0 weight percent of corn oil. The Experimental Groups I, II and III are maintained on the same diet as the Control Group except that 1-(3,5-di-tert-butyl-4-hydroxphenyl) methane is added to the extent of 0.3, 1.0 and 3.0 weight percent, based on the weight of the dog food, respectively. The compound is added by dessolving it in the corn oil up to the limit of solubility and thereafter thoroughly mixing any additional amount of compound with the dog food. After 30 days, samples of plasma and serum are taken and the serum analyzed for total lipid, total cholesterol, free cholesterol and cholesterol-ester values. The serum from the dogs in the Experimental Groups are found to contain significantly less total lipid, total cholesterol, free cholesterol and ester cholesterol than the serum from the dogs in the Control Group.

After 90 days of being maintained on the above diets, dogs in the Control Group and Experimental Groups are sacrificed and their plasma and serum are analyzed for cholesterol, phospholipid and triglyceride values. The serum from the dogs in the Experimental Groups are found to contain significantly less cholesterol, phospholipid and triglceride than the serum from the Control Group.

The amount of $\alpha$- and $\beta$-lipoprotain in the serum for each group is then determined by ultracentrifugation. The serum from the dogs in the Experimental Groups are found to contain significantly less $\alpha$-lipoprotein and $\beta$-lipoprotein than the serum from the control Group.

The compounds of this invention give outstanding reductions in all lipid and lipoprotein values, particularly in the $\beta$-lipoprotein values. High $\beta$-lipoprotein values are generally associated with atherosclerosis in man.

In addition to the above tests the nonsaponifiable fraction of the serum of the dogs in the Experimental Groups are analyzed for abnormal sterols such as desmosterol. No evidence of the presence of any abnormal sterol is found, showing that the effect of the compound on the biosynthesis of cholesterol is most likely at an earlier stage than after the cyclization of squalene. Such effects are highly desirable, as the formation of abnormal sterols may produce untoward side effects.

Efficacious results are also obtained with other compounds of this invention and other mammals such as cattle, sheep, rabbits, and others, and this invention is particularly desirable for treating humans.

In the above experiments, no untoward side effects are noted. Two pairs of pure bred male beagle dogs were fed diets containing 125 mg/kg and 35 mg/kg of (3,5-di-tert-butyl-4-oxo-2,5-cyclohexadien-1-ylidene)-(3,5-di-tert-butyl-4-hydroxyphenyl) methane (two dogs on each dose), respectively, for three months. The compound was dissolved in corn oil which comprised 5 percent by weight of the diet. Four control dogs received similar diets without the test compound. All were observed daily for clinical appearance, and food consumption and body weight were measured weekly. Pre-test bllod studies were performed three times for cholesterol, calcium, phosphorus, urea nitrogen, uric acid, total protein, total bilirubin, SGOT, alkaline phosphatase, glucose, hemoglobin, hematocrit, WBC, leucocyte differential, prothrombin time and bromsulfalein retention. At ½, 1, 2 and 3month intervals after the initiation of test diets, these pre-test studies were repeated except that the hemoglobin, hematocrit, WBC, leukocyte differential, prothrombin time, and bromsulfalein retention were repeated at 3 months only.

All dogs consumed their diets well, gained weight normally and did not exhibit any clinical illness. At 3 months the average serum cholesterol in the dogs receiving 125 mg/kg and 35 mg/kg of the test compound was reduced from the baseline average by 35 and 25 percent, respectively. An average 20 percent reduction was observed in the control dogs. There were no changes in the blood chemistries or blood counts aside from a questionable slight elevation of alkaline phosphatase.

An autopsy was performed on all animals. No significant gross abnormalities were noted. No drug induced changes were observed in the kidney, brain, adrenal, thyroid, or testes. Occasional vacuoles and swollen hepatic cells were seen in three of the four test animals (one animal of the high dose showed no changes). Similar changes were observed in control dogs.

The compounds are administered internally and may be parenterally or orally administered, the latter being preferable. The compounds of this invention are generally solid at room temperature and for oral administration pharmaceutical preparations of this invention may be made following conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of pharmaceutically acceptable inorganic materials which are known to be pharmaceutically safe and acceptable, as well as very convenient in preparing formulations. The compositions may take the form of tablets, linguets, powders, capsules, slurries, troches or lozenges, prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, distintegrating agents such as maize staren or alginic acid, and lubricating agents such as magnesium stearate may be used. A preferable tablet composition is one which comprises from about 10 to about 500 milligrams of (oxocyclohexadien-1-ylidene)-(hydroxyphenyl) methane, particularly (3,5-di-tert-butyl-4-oxo-2,5-cyclohexadien-1-ylidene)-(3,5-di-tert-butyl-4-hydroxyphenyl) methane.

If a liquid carrier is used, the preparation may be in the form of a soft gelatin capsule, a syrup a liquid solution or suspension. Many of the compounds of this invention are only slightly soluble in water, if at all, but are generally soluble in alcohols particularly glycols, to some extent. In general those (oxocyclohexadien-1-ylidene)-(hydroxyphenyl) methanes having greater hydrocarbon substitution are less soluble in water. The hydrocarbon solubility of most of the compounds of this invention is high enough to allow the use of various pharmaceutically-acceptable oils as carriers, For example vegetable or animal oils such as sunflower oil, safflower oil, maize oil or codliver oil can be used. Glycerine can also be used. With these latter solvents, from 25–30 percent water may be added. When water alone is the carrier, the preparation can be administered in the form of a slurry.

Emulsion compositions may be formulated using emulsifying agents such as sorbitan tri-eleate, polyoxyethylene sorbitan monoeleate, lecithin, gum acacia or gum tragacanth. Aqueous based suspensions may be prepared with the aid of wetting agents such as polyethylene oxide condensation products of alkylphenols, fatty alcohols or fatty acids and with suspending agents, for example a hydrophilic colloid such as polyvinylpyrrolidone. The emulsions and suspensions may contain conventional excipients such as sweeting agents, flowing agents, coloring materials and preservatives.

The compounds of this invention may be administered in the form of a nutritive preparation in which the mixture of active ingredients is mixed with proteins, such as casein and carbohydrates. In addition to the active ingredients, dietary supplements such as vitamins, salts of glycerophesphoric acid, choline, inositol and amino acids such as methionine may be added.

The percentage of (oxocyclohexadien-1-ylidene)-(hydroxyphenyl) methane in the pharmaceutical carrier may be varied. It is necessary that the (oxocyclehexadien-1-ylidene)-(hydroxyphenyl) methane constitute a preportion such that a suitable dosage will be obtained and it is preferred to use pharmaceutical compositions containing at least 10 weight percent of the (oxocyclohexadien-1-ylidene)-(hydroxyphenyl) methane. Activity increases with concentration of the agent in the carrier, but those compositions containing a significant amount of carrier, e.g. at least 1 percent and preferably at least 5 percent, are preferred as they allow for the easier administration of the (oxocyclohexadien-1-ylidene)-(hydroxyphenyl) methane.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle is desired. An 80 percent aqueous propylene glycol solution is a particularly convenient solvent system. A pH range, about 7.4, and isotonicity compatible with body isotonicity is desirable. Basicity may be controlled by addition of a base as required, and a particularly convenient base is monoethanolamine. It may often be desirable to incorporate a local anaesthetic and such are well known to those skilled in the art. For example, lidocaine ($\beta$-diethylamine-2,6-acetoxylidide) may be employed at a level of up to about 20 mg./c.c., or even more.

Administration of the compounds of this invention by the oral route is preferred. Advantageous daily dosages can be as low as 150 mg. for a human. A preferred range of daily dosage is about 1.5 to 7.5 grams. In terms of body weight, advantageous dosages are from 0.25 to 1000 mg. per kg. of body weight per day with a preferred range of about 2.5 to 1000 mg. per kg. of body weight per day. The daily dosage is preferably administered from one to four or five times daily in amounts of from about 150 mg. to about 2000 mg., and these amounts are administered in dosage units containing at least 10 mg. of the (oxocyclohexadien-1-ylidene)-(hydroxyphenyl) methane. For example, when administrating the compound in tablet form several tablets containing from, say 10 to 25 mg. of active compound can be administered, up to 4 or more times daily. Alternatively, larger dosage units containing more of the (oxocyclohexadien-1-ylidene)-(hydroxyphenyl) methane, say 50 to 500 mg., can be administered at less frequent intervals.

For parenteral applications daily dosages of about onetenth of that used for oral treatment are advantageous. Thus daily dosages can be as low as 15 mg. for a human, i.e., 0.25 mg. per kg. of body weight. A convenient upper limit is about 6 grams. From about 5 to about 1000 mg. per injection (dosage unit) in concentrations of about 5 to 200 mg/c.c, with from 1 to 3 injections of from 1 c.c. to 10 c.c. daily will give the required amount. Preferred formulations will contain from 50 to about 150 mg./c.c. to be given in one injection of from 1 c.c. to 5 c.c.

The oral or parenteral dose may be individually determined by the physician or veterinarian. Larger or smaller doses can be used and, in some cases, might be preferred in individual cases. Likewise administration need not be on a daily basis, although this is preferred, but may be, for example, on alternate days or even weekly and the like. With either oral or parenteral use, a daily regimen is preferred. However, even a single administration has some effect.

The following examples are not limiting but are illustrative of compounds and pharmaceutical preparations useful in this invention.

EXAMPLE 1

(3,5-di-tert-butyl-4-oxo-2,5-cyclohexadien-1-ylidene)-(3,5-di-tert-butyl-4-hydroxyphenyl)methane is compressed into tablets of 100 mg. each which can be administered orally as antihypercholesterolemic agents.

EXAMPLE 2

300 Mg. of [3-(1',1',3',3'-tetramethylbutyl)-5-methyl-4-oxo-2,5-cyclohexadien-1-ylidene]-[4-hydroxy-3-(1',1',3',3'-tetramethylbutyl)-5-methylphenyl]methane are filled into a No. 2 hard gelatin capsule.

EXAMPLE 3

200 Mg. of (3,5-di-sec-butyl-4-oxo-2,5-cyclohexadien-1-ylidene)-(3,5-di-sec-butyl-4-hydroxyphenyl)methane are mixed with 100 mg. of lactose and filled into a No. 2 hard gelatin capsule.

EXAMPLE 4

500 Mg. of (3,5-di-tert-butyl-4-oxo-2,5-cyclohexadien-1-ylidene)-(3,5-di-tert-butyl-4-hydroxyphenyl)-ethyl methane are compressed into a tablet.

EXAMPLE 5

10 Mg. of (3,5-di-tert-butyl-2-oxo-3,5-cyclohexadien-1-ylidene)-(3,5-di-tert-butyl-2-hydroxyphenyl)methane are compressed into a tablet.

EXAMPLE 6

50 Gms. of (3,5-di-tert-butyl-4-oxo-2,5-cyclohexadien-1-ylidene)-(3,5-di-tert-butyl-4-hydroxyphenyl) methane, 10 gms. of calcium sulfate and 25 gms. of sucrose are thoroughly mixed and granulated with hot 10 percent gelatin solution. The wetted mass is passed through a No. 16 U.S. standard mesh screen directly onto drying trays. The granules are dried at 120° F. and passed through a No. 20 U.S. standard mesh screen. These granules are then mixed with 15 gms. starch, 5 gms. talc and 3 gms. stearic acid, passed through a No. 60 U.S. standard mesh screen and then compressed into tablets containing 150 mg. of active ingredient.

EXAMPLE 7

75 Mg. of (4-oxo-2,5-cyclohexadien-1-ylidene)-(4-hydroxyphenyl) methane are mixed with 225 mg. of peanut oil to a thick slurry and filled into a soft gelatin capsule.

EXAMPLE 8

200 Gm. of (3-tert-butyl-5-methyl-4-oxo-2,5-cyclohexadien-1-ylidene)-(3-tert-butyl-4-hydroxy-5-methylphenyl)-methyl methane are thickly slurried in 250 gm. of safflower oil and the slurry is filled into soft gelatin capsules each of which contains 75 mg. of the active ingredient.

EXAMPLE 9

An oral composition is prepared as follows:
To 125 gms. of placebo granules composed of 64 percent lactose and 36 percent starch are added 100 gms. of (3-tert-butyl-5-methyl-2-oxo-3,5-cyclohexadien-1-ylidene)-(3-tert-butyl-5-methyl-2-hydroxyphenyl)methane. 15 Gms. of talc and 10 gms. of magnesium stearate are added. Tableting is done on a rotary machine.

EXAMPLE 10

Tablets are prepared with the following components:

| | |
|---|---|
| (3,5-di-tert-butyl-4-oxo-2,5-cyclohexadien-1-ylidene)-(3-tert-butyl-4-hydroxy-5-methylphenyl)methane, mg | 75 |
| Cornstarch, mg. | 40 |
| Lactose, mg. | 75 |
| Talc, mg. | 6 |
| Stearic Acid, mg. | 4 |
| Sugar coating, mg. approx. | 30 |

EXAMPLE 11

Tablets are prepared with the following components:

| | |
|---|---|
| (3-tert-butyl-5-methyl-4-oxo-2,5-cyclohexadien-1-ylidene)-(3,5-di-tert-butyl-4-hydroxyphenyl) methane, mg. | 60 |
| Confectioner's Sugar, mg. | 40 |
| Lactose, mg. | 50 |
| Talc, mg. | 4 |
| Stearic Acid, mg. | 5 |

EXAMPLE 12

Linguets are obtained by combining the following components:

| | |
|---|---|
| (3-tert-butyl-5-methyl-4-oxo-2,5-cyclohexadien-1-ylidene)-(3-tert-butyl-4-hydroxy-5-methylphenyl)-n-propyl methane, mg. | 25 |
| Lactose, mg. | 50 |
| Confectioner's sugar, mg. | 60 |
| Stearin, mg. | 2 |
| Talc, mg. | 13 |

EXAMPLE 13

| | |
|---|---|
| (2-oxo-3,5-cyclohexadien-1-ylidene-(2-hydroxyphenyl) methane, mg. | 300 |
| Magnesium Stearate, mg. | 10 |
| Lactose, mg. | 100 |

The above ingredients are screened, mixed and filled into hard gelatin capsules.

EXAMPLE 14

A mixture of 500 gms. of (3,5-di-tert-butyl-4-oxo-2,5-cyclohexadien-1-ylidene)-(3,5-di-tert-butyl-4-hydroxyphenyl) methane, 94 gms. of maine starch, 45 gms. of alginic acid and 3.5 gms. of magnesium stearate is compressed into slugs which are then broken into granules. The granules are sifted through an 8-mesh screen and 3.5 gms. of magnesium stearate are then added. The mixture is then compressed into tablets which are suitable for oral administration in accordance with the present invention.

EXAMPLE 15

To a mixture of 140 gms. of (3-cyclohexyl-4-oxo-5-phenyl-2,5-cyclohexadien-1-ylidene)-(3-cyclohexyl-4-hydroxy-5-phenylphenyl)-(m-ethylphenyl)methane and 33.7 gms. of corn oil are added 3 gms. of gum acacia and 1.5 gms. of gum tragacanth. To the thoroughly triturated mixture is added slowly with stirring a solution of 0.1 gms. of a cetyl alcohol polyoxyethylene condensate, 40 gms. of cane sugar, 0.03 gms. of propyl-p-hyroxybenzoate, 0.3 gms. of methyl-p-hydroxybenzoate, 0.002 gm. of edible dyestuff and 110 gms. of water. After the incorporation of a suitable flavoring agent, such as imitation wild cherry, the mixture is homogenized by passage through a conventional homogenizer and there is thus obtained an emulsion suitable for oral administration in accordance with the present invention. The emulsion is bottled in half-pint bottles.

EXAMPLE 16

100 Gms. of (3,5-di-tert-butyl-6-methyl-2-oxo-3,5-cyclohexadien-1-ylidene)-(3,5-di-tert-butyl-2-hydroxy-6-methylphenyl) methane are added to a solution of 15 gms. of calcium cyclamate, 2 gms. of a condensation product of octyloresol with 8–10 molecular proporations of ethylene oxide, 3 gms. of polyvinyl pyrolidone and 0.9 gms. of methyl-p-hydroxybenzoate in 100 gms. of water. The mixture is ball milled for several hours whereupon there is obtained a suspension suitable for oral administration in accordance with the present invention.

EXAMPLE 17

10 Gms. of (3-tert-butyl-5-ethyl-2-oxo-3,5-cyclohexadien-1-ylidene)- (3-tert-butyl-5-ethyl-2-hydroxyphenyl) methane are dissolved in a mixture of 83 gms. of water, 250 gms. glycerol and 125 gms. of ethyl alcohol. To the resultant solution is added a solution of 300 gms. of sucrose and 150 gms. of water. By the incorporation of a suitable flavoring agent and coloring material there is obtained a syrup suitable for oral administration in accordance with the present invention.

EXAMPLE 18

25 Gms. of sodium glycerophosphate, 25 gms. of calcium glycerophosphate and 50 gms. of (3,5-di-tert-butyl-4-oxo-2,5-cyclohexadien-1-ylidene)-(3,5-di-tert-butyl-4-hydroxyphenyl)-n-propyl methane are intimately mixed. The mixture is added gradually to 900 gms. of soluble casein in a conventional mixer and mixed until homogenous. There is thus obtained a dietary supplement suitable for oral administration in accordance with this invention.

EXAMPLE 19

An intimate mixture is prepared with conventional mixing equipment of 3 gms. of pyridoxine hydrochloride, 100 gms. of nicetinic acid, 100 gms. of nicotinamide, 5 gms. of methionine, 15 gms. of choline bitartrate, 150 gms. of ascorbic acid, 5 gms. of calcium pantothenate, 10 gms. of riboflavin and 100o gms. of (3,5-dicyclohexyl-4-oxo-2,5-cyclohexadien-1-ylidene)-(3,5-dicyclohexyl-4-hydroxyphenyl)methane. The mixture is filled into capsules which are then suitable for oral administration in accordance with this invention.

EXAMPLE 20

A mixture of 1 gm. of sodium dioctyl sulphosuccinate dissolved in a sufficient quantity of methanol, 500 gms. of (3,5-ditert-amyl-4-oxo-2,5-cyclohexadien-1-ylidene)-(3,5-di-tert-amyl-4-hydroxyphenyl)methane, 75 gms. of maize starch and 5 gms. of alginic acid is granulated by admixture with a sufficient quantity of aqueous 10 percent maize starch paste. the granules are passed through a 12-mesh screen and dried at 50° –55° C. The granules are then again passed through a 12-mesh screen and 6 gms. of magnesium stearate are added and the mixture is compressed into tablets containing 25 mg. of (3,5-di-tert-amyl-4-oxo-2,5-cyclohexadien-1-ylidene)-3,5-di-tert-amyl-4-hydroxyphenyl) methane. There are thus obtained tablets suitable for oral administration in accordance with this invention.

EXAMPLE 21

A mixture of 500 gms. of [3,5-di-($\alpha$-methylbenzyl)-4-hydroxyphenyl]methane, 50 gms. of light magnesium carbonate and 10 gms. of magnesium stearate is compressed into slugs. The slugs are broken into granules and passed through an 8-mesh screen and pressed into tablets containing 500 mg. of [3,5-di-($\alpha$-methylbenzyl)-4-oxo-2,5-cyclohexadien-1-ylidene]-[3,5-di-($\alpha$-methyl-benzyl)-4-hydroxyphenyl]methane. There are thus obtained tablets suitable for oral administration in accordance with this invention.

EXAMPLE 22

A mixture of 500 gms. of (3,5-di-tert-butyl-4-oxo-2,5-cyclohexadien-1-ylidene)-3,5-di-tert-butyl-4-hydroxyphenyl)-methyl methane, 94 gms. of maize starch and 3 gms. of magnesium stearate is compressed into slugs. The slugs are broken into granules which are then passed through an 8-mesh screen. The granules are then coated with a sufficient quantity of a mixture of 15 gms. of shellac and 3 gms. of castor oil in 800 gms. of ethyl alcohol. 3 Gms. of magnesium stearate are then added to the granules after which they are compressed to give tablets containing 150 mg. of (3,5-di-tert-butyl-4-oxo-2,5-cyclohexadien-1-ylidene)-(3,5-di-tert-butyl-4-hydroxyphenyl)-methyl methane and which are suitable for oral administration in accordance with this invention.

EXAMPLE 23

382 Gms. of propylene glycol are agitated for one hour while saturating with nitrogen gas. 12.4 Gms of (3,5-di-tert-butyl-4-oxo-2,5-cyclohexadien-1-ylidene)-(3,5-di-tert-butyl-4-hydroxyphenyl) methane are then added and the mixture is stirred for 30 minutes more.

Then 95 c.c of nitrogen saturated water is slowly added. After 5 minutes of further stirring 7.85 c.c. of monoethanolamine is added. Throughout the addition of ingredients the temperature is maintained below 30° C. by cooling as required. Solution is completed by stirring under nitrogen. The resulting 500 c.c. of clear, light-colored solution contains approximately 50 mg./c.c. of (3,5-di-tert-butyl-4-oxo-2,5-cyclohexadien-1-ylidene)-(3,5-di-tert-butyl-4-hydroxyphenyl) methane and is slightly alkaline. It is subdivided and samples are filled under nitrogen into 10 c.c. multi-dose vials sealed with butyl rubber stoppers. 3 C.C. doses can be withdrawn in the standard manner, by piercing the stopper with a hypodermic needle, injecting air and withdrawing the solution into the syringe. In this manner parenteral doses containing 150 mg. of (3,5-di-tert-butyl-4-oxo-2,5-cyclehexadien-1-ylidene)-(3,5-di-tert-butyl-4-hydroxyphenyl) methane are provided.

EXAMPLE 24

The procedure of Example 23 is followed except that 7.5 gms. of (3-tert-butyl-5-methyl-4-oxo-2,5-cyclohexadien-1-ylidene)-(3-tert-butyl-4-hydroxy-5-methylphenyl)-methyl methane is used in place of the (3,5-di-tert-butyl-4-oxo-2,5-cyclohexadien-1-ylidene)-(3,5-di-tert-butyl-4-hydroxyphenyl) methane. Sufficient nitrogen-saturated water is added to bring the volume to 500 c.c.'s. The resulting solution contains approximately 15.0 mg./c.c. of (3-tert-butyl-5-methyl-4-oxo-2,5-cyclohexadien-1-xlidene)-(3-tert-butyl-4-hydroxy-5-methylphenyl)-methyl methane. Subdividing the solution as in Example 22 allows the injection of 1 c.c. of solution containing 15.0 mg. of (3-tert-butyl-5-methyl-4-oxo-2,5-cyclohexadien-1-ylidene)-(3-tert-butyl-4-hydroxy-5-methylphenyl)-methyl methane.

Following the procedure of Example 23, pharmaceutical solutions suitable for intravenous and intramuscular administration are prepared according to the following formulations and packaged under nitrogen.

EXAMPLE 25

| | |
|---|---|
| (3-tert-butyl-5-methyl-4-oxo-2,5-cyclohexadien-1-ylidene)-(3-tert-butyl-4-hydroxy-5-methylphenyl)-n-propyl methane, gms. | 66.6 |
| Monoethanolamine, c.c. | 22.1 |
| Lidecaine, gm. | 10 |
| Propylene glycol, gm. | 275 |
| Water to make 400 c.c.'s. | |

The above solution contains 150 mgs./c.c. of (3-tert-butyl-5-methyl-4-oxo-2,5-cyclohexadien-1-ylidene)-(3-tert-butyl-4-hydroxy-5-methylphenyl)-n-propyl methane and can be administered intramuscularly in 1 c.c. doses, once a day, giving a daily dosage of 150 mgs.

EXAMPLE 26

| | |
|---|---|
| Glycerine, U.S.P., liter | 1 |
| (3,5-di-tert-butyl-4-oxo-2,5-cyclohexadien-1-ylidene)-(3,5-di-tert-butyl-4-hydroxyphenyl)-phenyl methane, gms. | 10 |
| Glycerine, U.S.P., to make 2 liters. | |

The above solution contains 5 mgs./c.c. of (3,5-di-tert-butyl-4-oxo-2,5-cyclohexadien-1-ylidene)-(3,5-di-tert-butyl-4-hydroxyphenyl)-phenyl methane and can be administered intravenously in three 1 c.c. dosage units to give a daily dosage of 15 mgs.

EXAMPLE 27

| | |
|---|---|
| Propylene glycol 300, c.c. | 200 |
| (3-tert-butyl-5-isopropyl-4-oxo-2,5-cyclohexadien-1-ylidene)-(3-tert-butyl-4-hydroxy-5-isopropylphenyl) methane | 400 |
| Triethanolamine, c.c. | 25 |
| Propylene glycol 300, to make 1 liter. | |

The above solution contains 250 mgs./c.c. of (3-tert-butyl-5-isopropyl-4-oxo-2,5-cyclohexadien-1-ylidene)-(3-tert-butyl-4-hydroxy-5-isopropylphenyl)methane and can be administered 3 times a day in 5 c.c. doses to give a daily dosage of 6000 mgs.

EXAMPLE 28

| | |
|---|---|
| Glycerine, U.S.P., c.c. | 500 |
| (3-cyclohexyl-5-methyl-4-oxo-2,5-cyclohexadien-1-ylidene)-(3-cyclohexyl-4-hydroxy-5-methylphenyl) methane | 100 |
| 10 per cent sodium hydroxide in glycerine to Ph 7.4 | |
| Glycerine, U.S.P., to make 1 liter. | |

The above solution contains 100 mgs./c.c. of (3-cyclohexyl-5-methyl-4-oxo-2,5-cyclohexadien-1-ylidene)-(3-cyclohexyl-4-hydroxy-5-methylphenyl) methane and can be administered intravenously 2 times a day in 5 c.c. doses to give a daily dosage of 1000 mgs.

EXAMPLE 29

| | |
|---|---|
| Glycerine, U.S.P., c.c. | 500 |
| Sorbitol, gm. | 50 |
| (3,5-di-tert-butyl-4-oxo-2,5-cyclohexadien-1-ylidene)-(3,5-di-tert-butyl-4-hydroxyphenyl)-methyl methane, gms. | 50 |
| Glycerine, U.S.P., to make 1 liter. | |

The above solution contains 50 mg./c.c. of (3,5-di-tert-butyl-4-oxo-2,5-cyclohexadien-1ylidene)-(3,5-di-tert-butyl-4-hydroxyphenyl)-methyl methane.

EXAMPLE 30

| | |
|---|---|
| Propylene glycol, c.c. | 800 |
| (3-tert-butyl-5-methyl-4-oxo-2,5-cyclohexadien-1-ylidene)-(3-tert-butyl-4-hydroxy-5-methylphenyl)-phenyl methane, gm. | 90 |
| Benzocaine, gm. | 51 |
| Propylene glycol, to make 1 liter. | |

The above solution contains 90 mgs./c.c. of (3-tert-butyl-5-methyl-4-oxo-2,5-cyclohexadien-1-ylidene)-(3-tert-butyl-4-hydroxy-5-methylphenyl)-phenyl methane.

EXAMPLE 31

| | |
|---|---|
| Glycerine, U.S.P., c.c. | 500 |
| 70 per cent aqueous sorbitol, gm. | 100 |
| [3-(α-methylbenzyl)-5-tert-butyl-4-oxo-2,5-cyclohexadien-1-ylidene]-[3-(α-methylbenzyl)-5-tert-butyl-4-hydroxyphenyl] methane gm. | 60 |
| Ethanol, c.c. | 80 |
| Glycerine, U.S.P., to make 1 liter. | |

The above solution contains 60 mg./c.c. of [3-(α-methylbenzyl)-5-tert-butyl-4-oxo-2,5-cyclohexadien-1-ylidene]-[3-(α-methylbenzyl)-5-tert-butyl-4-hydroxyphenyl] methane.

EXAMPLE 32

| | |
|---|---|
| (3-tert-butyl-5-methyl-4-oxo-2,5-cyclohexadien-1-ylidene)-(3-tert-butyl-4-hydroxy-5-methylphenyl) methane, gms. | 25 |
| Glycerine, U.S.P., to make 1 liter. | |

The above solution contains 25 mg./c.c. of (3-tert-butyl-5-methyl-4-oxo-2,5-cyclohexadien-1-ylidene)-(3-tert-butyl-4-hydroxy-5-methyl-phenyl) methane.

It is to be understood that mixtures of the compounds of this invention can be used although it is preferred to use discreet compounds.

The (2-oxo-3,5-cyclohexadien-1-ylidene)-(hydroxyphenyl) methanes of this invention are new compounds and form another embodiment of this invention. They can be prepared by oxidation, as described above, of the corresponding (2-hydroxyphenyl)-(hydroxyphenyl) methane, which in turn can be prepared by base condensation of appropriate phenols with an appropriate aldehyde, followed by separation, where necessary, using appropriate separation procedures. The following examples, in which all parts are by weight, illustrate the preparation of (2-oxo-3,5-cyclohexadien-1-ylidene)-(hydroxyphenyl) methanes of this invention.

EXAMPLE 33

In a reaction vessel equipped with stirring means, condensing means, thermometer and reagent introducing means are placed a solution of 6.6 parts of potassium hydroxide dissolved in 400 parts of isopropanol. To this stirred solution is added 103 parts of 2,6-tert-butylphenol and 103 parts of 2,4-di-tert-butylphenol. At a temperature of 30° C. a total of 45.4 parts of 37 percent formalin solution is added dropwise. The mixture is heated to 60° C. and stirred at that temperature for 1½ hours, cooled and solids filtered off. The solids, composed of a mixture of di-(3,5-di-tert-butyl-4-hydroxyphenyl) methane, di-(3,5-di-tert-butyl-2-hydroxyphenyl) methane and (3,5-di-tert-butyl-2-hydroxyphenyl)-(3,5-di-tert-butyl-4-hydroxyphenyl) methane are separated by fractional crystallization from n-hexane into the discreet compounds.

Five parts of di-(3,5-di-tert-butyl-2-hydroxyphenyl) methane are added to a reaction vessel equipped with stirring means, thermometer, reagent introducing means and gas inlet and outlet tubes and containing 125 parts of glacial acetic acid. The reaction vessel is flushed with nitrogen and 0.5 part of bromine in 10 parts of glacial acetic acid is gradually added with stirring. The solution is left at about 20° C, under a nitrogen atmosphere for about 2 hours. Then di-(3,5-di-tert-butyl-2-hydroxyphenyl) bromomethane is collected on a filter stick (under nitrogen atmosphere) and quickly transferred to a dessicator and dried under reduced pressure.

Three tenths of a part of the di-(3,5-di-tert-butyl-2-hydroxyphenyl) bromomethane produced above is dissolved in 20 parts of ethanol and placed in the reaction vessel just above described. One part of 5 percent aqueous sodium hydroxide solution is added and a slow current of nitrogen is passed through the solution for 20 minutes. The reaction mixture is poured into a vessel containing crushed ice, neutralized with acetic acid and extracted with ether. The ether is evaporated and the residue crystallized twice from aqueous ethanol to yield (3,5-di-tert-butyl-2-oxo-3,5-cyclohexadien-1-ylidene)-(3,5-di-tert-butyl-2-hydroxyphenyl) methane.

Ten and six tenths part of the (3,5-di-tert-butyl-2-hydroxyphenyl)-(3,5-di-tert-butyl-4-hydroxyphenyl) methane produced above are added to a reaction vessel equipped with stirring means, thermometer, reagent introducing means and gas inlet and outlet tubes and containing 250 parts of glacial acetic acid. The reaction vessel is flushed with nitrogen and 1.0 part of bromine in 20 parts of glacial acetic acid is gradually added with stirring. The solution is left at about 20° C., under a nitrogen atmosphere, for about 2 hours. Then (3,5-di-tert-butyl-2-hydroxyphenyl)-(3,5-di-tert-butyl-4-hydroxyphenyl) bromomethane is collected on a filter stick (under nitrogen atmosphere) and quickly transferred to a dessicator and dried under reduced pressure.

Six tenths of a part of the (3,5-di-tert-butyl-2-hydroxyphenyl)-(3,5-di-tert-butyl-4-hydroxyphenyl) bromomethane produced above is dissolved in 40 parts of ethanol and placed in the reaction vessel just above described. Two parts of a 5 percent aqueous sodium hydroxide solution is added and a slow current of nitrogen is passed through the solution for 20 minutes. The reaction mixture is poured into a vessel containing crushed ice, neutralized with acetic acid and extracted with ether. The ether is evaporated and the resulting solids are fractionally crystallized from aqueous ethanol to yield, separately, (3,5-di-tert-butyl-2-oxo-3,5-cyclohexadien-1-ylidene)-(3,5-di-tert-butyl-4-hydroxyphenyl) methane and (3,5-di-tert-butyl-4-oxo-2,5-cyclohexadien-1-ylidene)-(3,5-di-tert-butyl-2-hydroxyphenyl) methane.

I claim:

1. A method of lowering plasma lipid levels in a mammal which comprises internally administering to said mammal from about 0.25 mg to about 1.0 grams of a compound having the formula

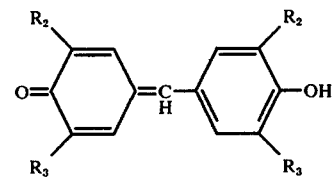

wherein $R_2$ is alpha-branched alkyl of from 3–12 carbon atoms and $R_3$ is alkyl of from 1–12 carbon atoms; per kilogram of body weight per day.

2. The method of claim 1 which comprises oral administration.

3. The method of claim 2 which comprises orally administering from about 2.5 milligrams to about 125 milligrams of (3,5-di-tert-butyl-4-oxo-2,5-cyclohexadien-1-ylidene)-(3,5-di-tert-butyl-4-hydroxyphenyl)methane per kilogram of body weight per day.

4. The method of lowering plasma lipid levels in a mammal which comprises internally administering to said mammal from about 0.25 milligram to about 1.0 grams of (3,5-di-tert-butyl-4-oxo-2,5-cyclohexadien-1-ylidene)-(3,5-di-tert-butyl-4-hydroxyphenyl)methane per kilogram of body weight per day.

5. A therapeutic composition in dosage unit form for reducing plasma lipid levels comprising from about 10 milligrams to about 500 milligrams of (3,5-di-tert-butyl-4-oxo-2,5-cyclohexadien-1-ylidene)-(3,5-di-tert-butyl-4-hydroxyphenyl)methane and a solid, inorganic pharmaceutical carrier.

6. A therapeutic composition in dosage unit form for reducing plasma lipid levels comprising from about 10 milligrams to about 500 milligrams of (3,5-di-tert-butyl-4-oxo-2,5-cyclohexadien-1-ylidene)-(3,5-di-tert-butyl-4-hydroxyphenyl) methane in tablet form.

* * * * *